United States Patent [19]
Katz

[11] Patent Number: 5,420,382
[45] Date of Patent: May 30, 1995

[54] SEA-SHELL STETHOSCOPE HEAD

[76] Inventor: Daniel B. Katz, 9979 Nob Hill La., Sunrise, Fla. 33351

[21] Appl. No.: 185,687

[22] Filed: Jan. 24, 1994

[51] Int. Cl.$^6$ ............................................. A61B 7/02
[52] U.S. Cl. ................................................... 181/131
[58] Field of Search .................... 181/131, 137, 132; 381/67

[56] References Cited

U.S. PATENT DOCUMENTS

| | | | |
|---|---|---|---|
| 977,503 | 12/1910 | Baylis | 181/131 |
| 1,321,266 | 11/1919 | Wilkinson | 181/131 |
| 2,515,471 | 7/1950 | Ratzan | 181/131 |
| 3,493,075 | 2/1970 | Mendelson et al. | 181/131 |

Primary Examiner—Howard B. Blankenship
Assistant Examiner—Khanh Dang
Attorney, Agent, or Firm—Malin, Haley, DiMaggio & Crosby

[57] ABSTRACT

The invention is an improved stethoscope head having a conical shell-like head for improved acoustic detection and transmission. In its preferred embodiment, a stethoscope head may be constructed from a sea shell having a relatively broad, generally circular aperture defining a sound chamber opening, said chamber having a naturally polished, sound reflecting, interior surface. The interior surface defines a conical acoustic chamber having a generally helical axis resulting in a deep, yet compact chamber which increases the effective sound power radiated along the axis as acoustic waves propagate thereby functioning as an acoustic transformer and enhancing the fidelity of the received signal while masking unwanted sounds produced by the anatomy.

6 Claims, 3 Drawing Sheets

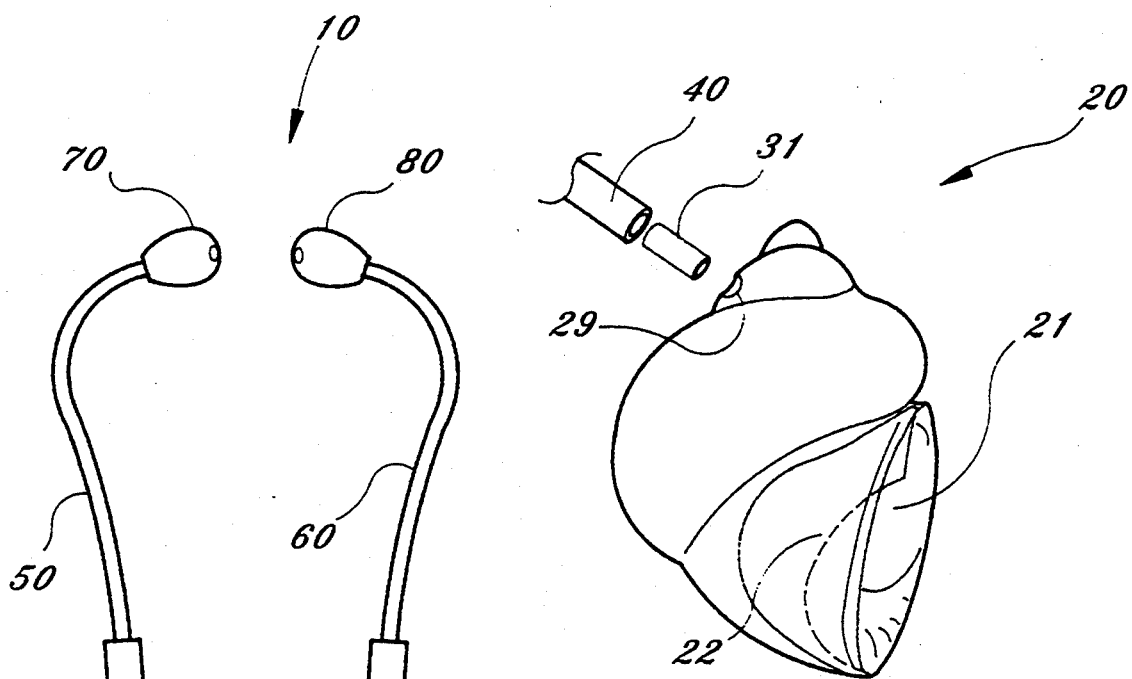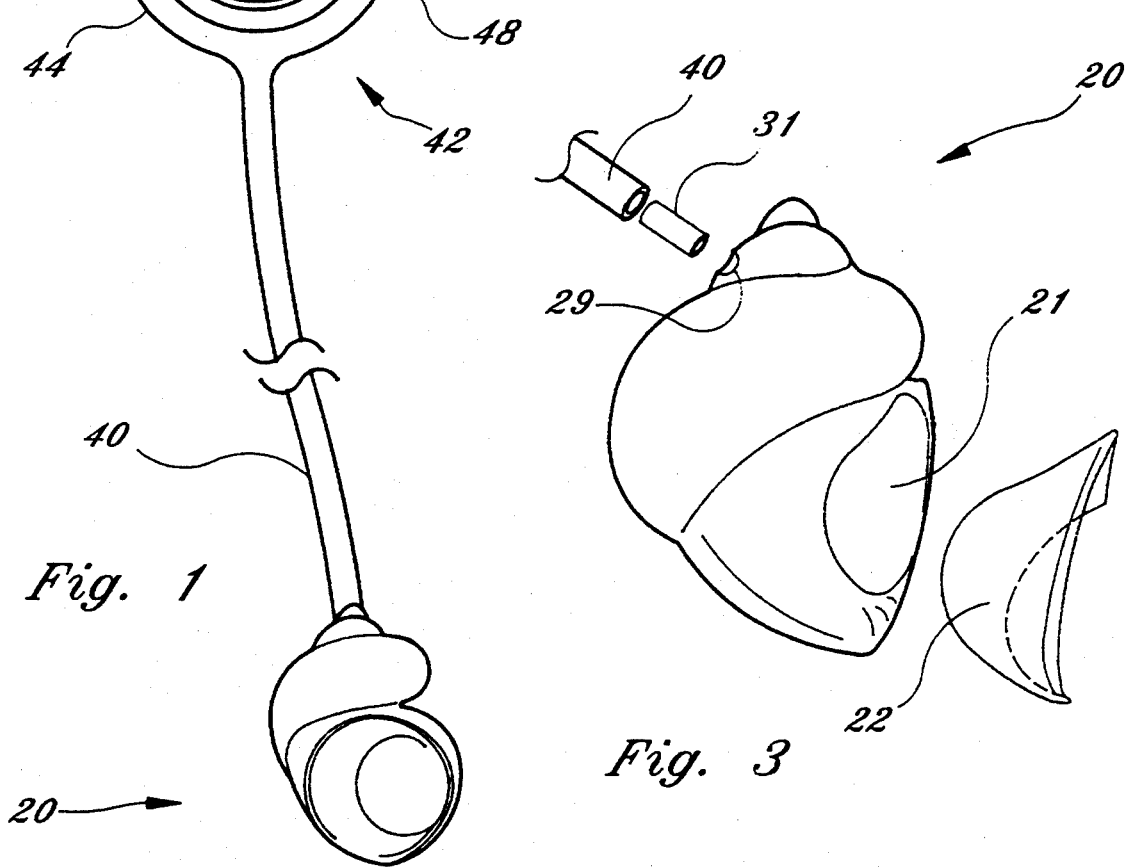
Fig. 1
Fig. 2
Fig. 3

SEA-SHELL STETHOSCOPE HEAD

BACKGROUND OF THE INVENTION

1. Field of the Invention

This invention relates to the field of acoustical listening devices. More particularly, the instant invention relates to an improved stethoscope head having a sound enhancing conical shell-like acoustic chamber.

2. Description of the Prior Art

Medical stethoscopes are commonly used in the health care field to detect and transmit biological sounds made by the human body. These sounds are used by the medical practitioner in diagnosing a wide variety of problems including those of the heart and lungs. The act of listening to sounds arising within organs as an aid to diagnosis and treatment is called auscultation. The medical practitioner compares the sounds perceived while auscultating the patient to those considered "normal" and thereby assesses the patients physical condition. Therefore, it is important for a stethoscope to accurately transmit the sounds detected to the medical practitioner as to enable him to accurately assess the patients condition.

The human body produces sounds across a broad spectrum of frequencies. Low-frequency (20 to 80 Hz) sound waves are common to both normal and pathological heart and lung activity, while higher frequency (80 to 800 Hz) sound waves are produced by certain murmurs and abnormal lung conditions. As a result, the human body simultaneously produces sounds across this broad spectrum making if difficult for the medical practitioner to distinguish between sounds produced by particular parts of the anatomy.

A number of stethoscope designs attempt to provide increased sensitivity to sound waves existing on either the high or low end of the frequency spectrum. These efforts have resulted in the development of two types of stethoscope heads, commonly referred to as the bell type and the diaphragm type. It has been found that the bell type stethoscope head provides greater sensitivity to low frequency sounds, while the diaphragm type stethoscope head provides greater sensitivity to higher frequency sounds. Furthermore, it has been found that as a bell chamber depth increases, its performance improves. Bell chamber depth, however, has been limited by the practical need for a compact and lightweight stethoscope head.

The prior art reveals an effort to incorporate both type of heads into a common stethoscope head body. However, incorporating both devices into a single stethoscope head has proven difficult, resulting in bulky and intricate devices that often do not allow the medical practitioner to simultaneously listen to both high and low frequency sounds. Therefore, there exists a need for an improved stethoscope head capable of delivering an optimum balance of low and high frequency sounds; also there exists a need for a stethoscope head that detects sounds produced by the heart while masking unwanted background sounds.

The prior art reveals a number of such complicated designs which provide a dual stethoscope head incorporating both bell type and diaphragm type heads. Since these inventions are often limited in the sense that the bell and diaphragm components function independently and are not capable of simultaneous operation, the inventions often do not permit the medical practitioner to simultaneously hear both low and high frequency sounds.

For example, U.S. Pat. No. 3,951,230 issued to Littmann discloses a multi-chamber stethoscope wherein a diaphragm sound chamber is disposed within a housing which allows for the head to be used independently as a diaphragm sound chamber or a bell sound chamber. Incorporating both heads into a single unit of acceptable size requires compromising performance as available chamber space is limited. In addition, combining both heads in sliding engagement requires tight tolerances and an abundance of hardware greatly complicating manufacturing costs and further compromising performance.

U.S. Pat. No. 4,212,368 issued to Allen suffers from similar flaws. The Allen patent discloses a stethoscope head having a bell and a diaphragm, the bell axis intersecting the diaphragm axis at an acute angle, and a selectively movable valve provided to connect the bell and the diaphragm, individually, to the sound tube. This arrangement also does not permit the medical practitioner to simultaneously hear both high and low frequency sounds. Furthermore, this design requires an abundance of intricate hardware and movable components that increase cost and adversely affect reliability and performance.

U.S. Pat. No. 4,903,794 issued to Klippert, discloses a stethoscope head incorporating a curvilinear convex diaphragm for interfacing with the site being auscultated, and an enclosed acoustic chamber for enhancing the fidelity of the received sounds. While the Klippert invention does allow the medical practitioner to listen to a broad spectrum of sound, it requires the use of machined enclosed acoustical chambers which require extreme manufacturing tolerances and are thus costly to fabricate.

As has been described, incorporating two different auscultating devices into a single stethoscope head has proven difficult, and resulted in bulky and intricate devices that, by enhancing sounds at extreme ends of the frequency spectrum, only allow the medical practitioner to listen to sounds within a relatively narrow frequency range. Therefore, there exists a need for an improved stethoscope head capable of delivering an optimum balance of low to high frequency sounds, thus providing the medical practitioner with a complete sound profile while masking unwanted background sounds.

SUMMARY OF THE INVENTION

The present invention discloses a stethoscope head which eliminates the prior art deficiencies described. The instant invention contemplates an improved stethoscope comprised of a shell-like stethoscope head incorporating a deep, yet compact, cylindrical conical shell acoustic chamber which communicates with a sound tube terminating in a pair of conventional ear tips.

In the preferred embodiment of the present invention, a stethoscope head may be constructed from a common sea shell of the Turbinidae or Trochidae families, having a relatively broad, generally circular aperture defining an acoustic chamber opening, said chamber having a naturally polished, sound reflecting interior surface. The polished interior surface defines a substantially conical acoustic chamber having a generally helical axis resulting in a deep, yet compact, chamber. The chamber increases the effective sound power radiated along the axis as acoustic waves propagate thereby functioning as an acoustic transformer and enhancing the intensity of the received signal. An air passage, defined by a sound tube, is fixedly connected to the acoustic chamber near its apex thus allowing the passage of intensified acoustical waves into the sound tube leading to the aural interface at the bifurcated tips.

The foregoing sound propagation theory describes the sound field at a distance from the source, and is known as ray acoustics. According to this theory, a sound ray is a line drawn normal to the wave front of the sound travels. A principle relation being that the power flow remains constant along a ray tube of constant cross sectional area. Therefore, as the cross sectional area of the acoustic chamber decreases, the effective sound power or intensity increases.

The acoustical properties derived from the natural structure of common sea-shells make the present invention of particular significance to developing regions of the world that neither possess the wealth nor manufacturing sophistication to acquire or produce the sophisticated stethoscopes currently available. The instant invention provides an alternative, high quality compact bell chamber, that may be converted to a functioning medical instrument with only minor modification.

Furthermore, it has been found that the shell stethoscope head of the instant invention allows the medical practitioner to more easily discriminate sounds produced by the heart from those produced by other parts of the anatomy. This advantage is maximized when the instant invention is used on the pediatric or comatose patient, or on any other patient who cannot cooperate with the medical practitioner to momentarily stop breathing while the practitioner auscultates.

Due to the shortcomings present in prior art stethoscope systems, it is a principle object of the instant invention to provide an improved stethoscope.

It is also an object of the instant invention to provide an improved stethoscope head capable of delivering an optimum balance of low to high frequency sounds.

An additional object of the instant invention is to provide a stethoscope head having a large yet compact acoustic chamber.

Still another object of the instant invention is to provide a stethoscope head sound chamber capable of focusing acoustic waves.

A further object of the instant invention is to provide a low cost stethoscope delivering high acoustic performance.

Still another object of the instant invention is to provide a naturally polished acoustic chamber found abundantly in nature and capable of use as a high quality stethoscope head.

A further object of the instant is to provide a stethoscope that allows a medical practitioner to distinguish cardiovascular sounds from the sounds produced by other parts of the anatomy.

In accordance with these and other objects which will become apparent hereinafter, the instant invention will now be described with particular reference to the accompanying drawings.

BRIEF DESCRIPTION OF THE DRAWINGS

FIG. 1 depicts a perspective illustration of a stethoscope employing the instant invention as embodied using a Turbinidae family shell.

FIG. 2 depicts a perspective illustration of the shell-like stethoscope head.

FIG. 3 depicts a an exploded view of the shell-like stethoscope head highlighting a synthetic piece fitted to the contoured chamber opening.

DESCRIPTION OF THE PREFERRED EMBODIMENTS

Figures 6, 7:
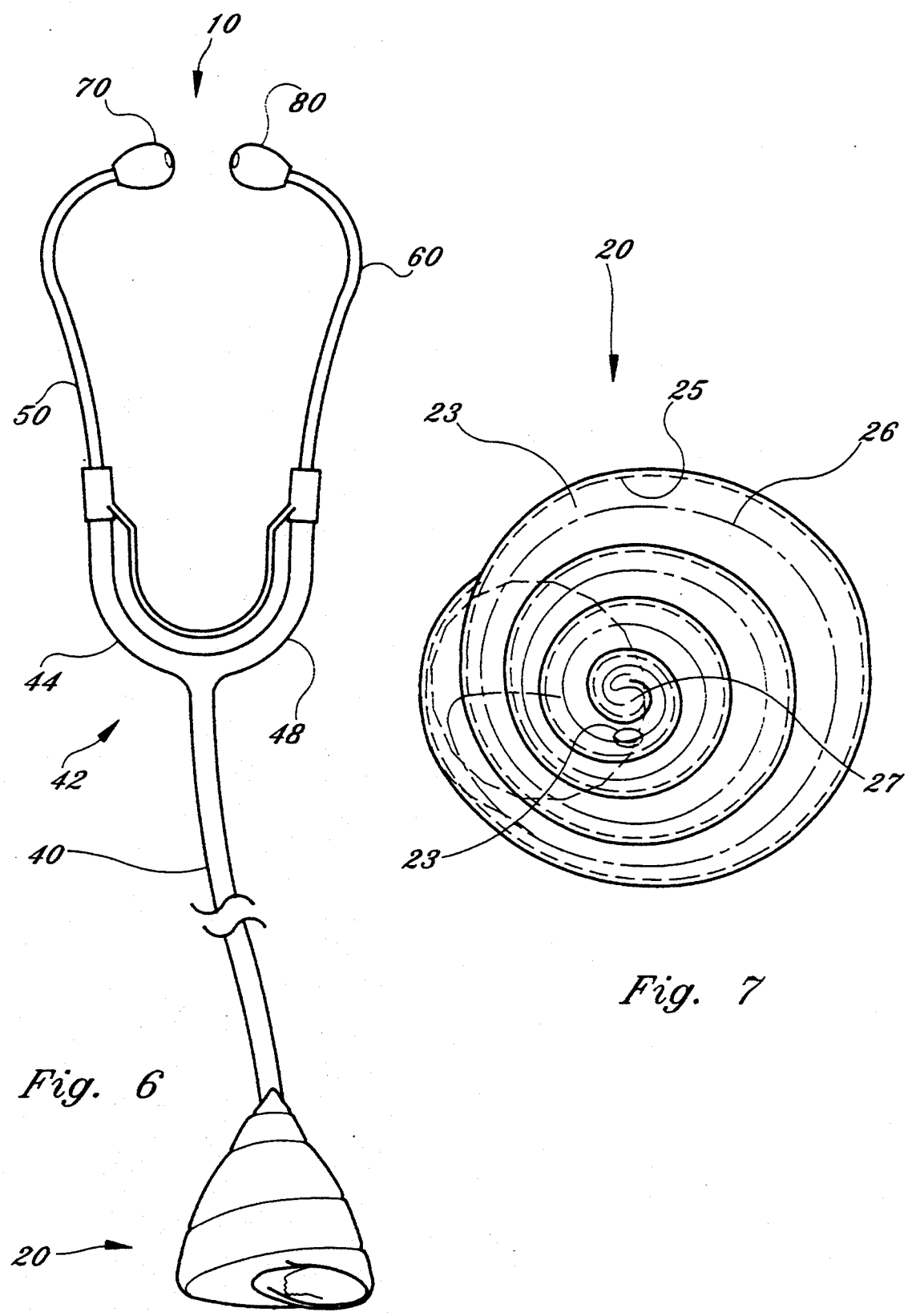
FIG. 6 depicts a perspective illustration of a stethoscope employing the instant invention as embodied using a Trochidae family shell.
FIG. 7 depicts a plan view of the shell stethoscope head embodied by a Trochidae family shell.

FIGS. 1 and 6 depict alternate embodiments of the instant invention incorporating Turbinidae and Trochidae family shells respectively. FIGS. 1 and 6 each depict in perspective view the improved stethoscope of the instant invention generally designated as 10. The stethoscope includes a stethoscope head 20 in acoustical communication with a sound tube 40 which terminates in a binaural yoke 42. Binaural yoke 42 includes sections 44 and 48 which are in acoustical communication with tubing 50 and 60, said tubing 50 and 60 terminating in aural interfaces 70 and 80 respectively. It should be noted here that acoustical tubing 40, 42, 50 and 60 as well as aural interfaces 70 and 80 are well known in the art, and the instant invention is suitable for use with acoustical communication tubing other than that now described.

Referencing now to FIG. 2, there is depicted the Turbindae shell stethoscope head 20 of the instant invention. In its preferred embodiment, said stethoscope head body 20 is comprised of a sea shell, of the Turbinidae family, a sea shell found abundantly in shallow tropical waters. The stethoscope head 20, incorporates a naturally formed first aperture 21 defining a sound chamber opening, and a synthetic wedge 22 rigidly attached to the shell body 20 and matingly joined with said first aperture 21 and contoured with said naturally formed first aperture 21 as to form a generally planar circular opening for interfacing with a patient in a conventional manner.

Figure 4:
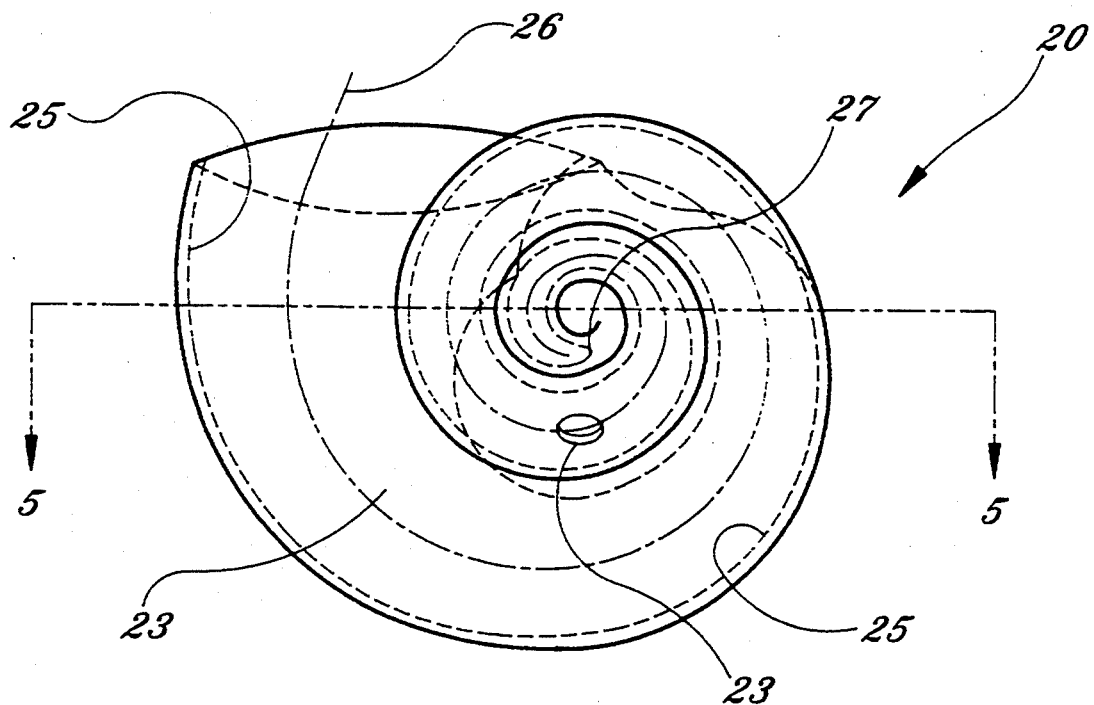
FIG. 4 depicts a plan view of the shell stethoscope head embodied by a Turbinidae family shell.
Figure 5:
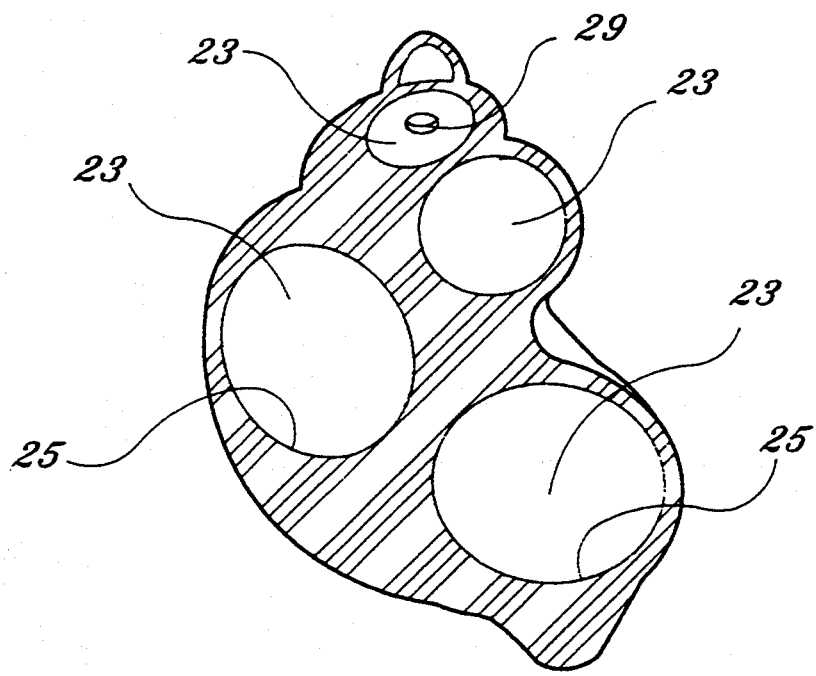
FIG. 5 depicts a sectional view of as indicated in FIG. 4 of the shell-like stethoscope head as embodied by a Turbinidae family shell.

As is best depicted in FIGS. 4 and 5, and in FIG. 7 for an alternate embodiment constructed from a Trochidae family shell, the stethoscope head further incorporates a sound chamber 23 defined by said first aperture 21 and a naturally polished, generally conical interior surface 25. Said sound chamber 23 has a substantially helical chamber axis 26 such that said sound chamber terminates at an apex 27. The resulting reduction in chamber cross sectional area increases the effective sound power radiated along the axis as acoustic waves propagate thereby functioning as an acoustic transformer and enhancing the fidelity of the received signal. The described arrangement yields a deep acoustic chamber, resulting in optimum performance, while maintaining a compact and light-weight stethoscope head.

The stethoscope head further incorporates a machined second aperture 29 on said body 20, substantially adjacent said apex 27, and defining an air passage thus allowing the passage of acoustical waves from the sound chamber 23. As is best depicted in FIG. 2, a tubular connector 31, having an outside diameter slightly less than said second aperture 29, is disposed and sealed within said second aperture 29, partially extending outward from said body 20 as to form a ducted passage for acoustical waves. The sound tube 40, is coupled to the connector 31 in a similar airtight manner such that said sound tube 30 is in direct acoustical communication with the sound chamber 23. The air passage, defined by the sound tube 40, thus allows the passage of acoustical waves into the sound tube leading to the aural interface at the bifurcated tips.

While the aforementioned described embodiments utilize seashells harvested from the sea, it is also contemplated that the instant invention may be practiced utilizing a variety of other materials. As a result the instant invention contemplates the use a variety of synthetic materials including, but not limited to, metals, plastics, or ceramics. It is further contemplated that the described shell-like structure may be produced using alternate materials by various manufacturing techniques such as injection molding, forging, or other suitable technique.

The instant invention functions as a conventional bell chamber stethoscope, and it is contemplated that the aperture 21 defining the sound chamber opening may be adapted by attachment of a diaphragm such that the invention functions as a conventional diaphragm type stethoscope.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A stethoscope having a synthetic sea-shell stethoscope head in acoustical communication with conventional ear pieces, for use in auscultating sounds comprising:
    a synthetic sea-shell body having an opening, said opening forming an acoustic passageway to an acoustic chamber housed within said synthetic sea-shell body, said acoustic chamber defined by an interior sea-shell wall;
    interface means, connected to said synthetic sea-shell body opening, for forming an auscultation interface between said acoustic chamber and a patient for detecting sounds generated by the patient's body;
    said acoustical chamber and said interior sea-shell wall comprising a means for intensifying said detected sounds; and,
    acoustical communication means, acoustically interfaced with said acoustical chamber, for communication of intensified sound waves from said acoustical chamber to a listener via conventional ear pieces, wherein said communication means comprises, an aperture existing on said sea-shell body, forming an acoustic passageway for the communication of acoustic waves from said chamber to said listener.

2. A stethoscope having a sea-shell stethoscope head in acoustical communication with conventional ear pieces, for use in auscultating sounds comprising:
    a sea-shell body having an opening, said opening forming an acoustic passageway to an acoustic chamber housed within said sea-shell body;
    interface means, connected to said sea-shell body opening, for forming an auscultation interface between said acoustic chamber and a patient being auscultated whereby sound waves are detected; and,
    acoustical communication means, acoustically integrated with said interface means, for communicating said detected sound waves from said seashell body to a listener via a conventional pair of ear pieces.

3. A sea-shell stethoscope head according to claim 2, wherein said interface means comprises a contoured synthetic wedge connected to said sea-shell body and matingly joined with said sea-shell body opening thereby forming a generally planar circular acoustic chamber opening.

4. A sea-shell stethoscope head according to claim 2, wherein said sea-shell is of the Turbinidae family.

5. A sea-shell stethoscope head as defined in claim 2, wherein said sea-shell is of the Trochidae family.

6. A stethoscope having a sea-shell stethoscope head in acoustical communication with conventional ear pieces, for use in auscultating sounds comprising:
    a sea-shell body forming a stethoscope head;
    said sea-shell body having a naturally formed aperture defining an acoustical passageway to a generally conical acoustic chamber housed within said sea-shell body, said acoustic chamber defined by a converging interior sea-shell wall terminating at a chamber apex;
    interfacing means, connected to said sea-shell body aperture, for forming an auscultation seal between said acoustical chamber and a patient for detecting sounds generated by the patient's body, wherein said interfacing means comprises a contoured synthetic wedge connected to said sea-shell body and matingly joined with said naturally formed aperture;
    said acoustic chamber and said interior sea-shell wall comprising a means for enhancing the intensity of said detected sounds;
    acoustical communication means, acoustically interfaced with said acoustic chamber, for communication of said enhanced acoustic sound waves from said chamber to a listener via conventional ear pieces wherein said communication means comprises a second aperture existing on said sea-shell body adjacent to said chamber apex, thereby forming a passageway for the communication of acoustic sound waves from said chamber.

* * * * *